US006878559B2

(12) United States Patent
Borden et al.

(10) Patent No.: US 6,878,559 B2
(45) Date of Patent: Apr. 12, 2005

(54) MEASUREMENT OF LATERAL DIFFUSION OF DIFFUSED LAYERS

(75) Inventors: Peter G. Borden, San Mateo, CA (US); G. Jonathan Kluth, Los Gatos, CA (US); Eric Paton, Morgan Hill, CA (US)

(73) Assignees: Applied Materials, Inc., Santa Clara, CA (US); Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 10/253,121

(22) Filed: Sep. 23, 2002

(65) Prior Publication Data

US 2004/0063225 A1 Apr. 1, 2004

(51) Int. Cl.[7] .............................................. H01L 21/66
(52) U.S. Cl. ............................ 438/14; 438/15; 438/16; 324/765; 356/432
(58) Field of Search ............................. 438/14, 15, 16; 324/765; 356/432

(56) References Cited

U.S. PATENT DOCUMENTS

| | | | | |
|---|---|---|---|---|
| 4,571,685 A | * | 2/1986 | Kamoshida | ................. 700/108 |
| 4,978,627 A | * | 12/1990 | Liu et al. | ...................... 438/14 |
| 5,159,412 A | * | 10/1992 | Willenborg et al. | ........ 356/445 |
| 5,181,080 A | * | 1/1993 | Fanton et al. | ................ 356/632 |
| 5,228,776 A | * | 7/1993 | Smith et al. | .................... 374/5 |
| 5,379,109 A | * | 1/1995 | Gaskill et al. | .............. 356/445 |
| 6,274,449 B1 | * | 8/2001 | Vasanth et al. | ............. 438/305 |
| 6,649,429 B1 | * | 11/2003 | Adams et al. | ................ 438/14 |
| 6,694,284 B1 | | 2/2004 | Nikoonahad et al. | ....... 702/155 |
| 6,734,968 B1 | | 5/2004 | Wang et al. | ................ 356/369 |

* cited by examiner

Primary Examiner—John F. Niebling
Assistant Examiner—Olivia T. Luk
(74) Attorney, Agent, or Firm—Silicon Valley Patent Group LLP

(57) ABSTRACT

Any semiconductor wafer fabrication process may be changed to monitor lateral abruptness of doped layers as an additional step in the wafer fabrication process. In one embodiment, a test structure including one or more doped regions is formed in a production wafer (e.g. simultaneously with one or more transistors) and one or more dimension(s) of the test structure are measured, and used as an estimate of lateral abruptness in other doped regions in the wafer, e.g. in the simultaneously formed transistors. Doped regions in test structures can be located at regularly spaced intervals relative to one another, or alternatively may be located with varying spacings between adjacent doped regions. Alternatively or in addition, multiple test structures may be formed in a single wafer, with doped regions at regular spatial intervals in each test structure, while different test structures have different spatial intervals.

19 Claims, 9 Drawing Sheets

FIG. 4A
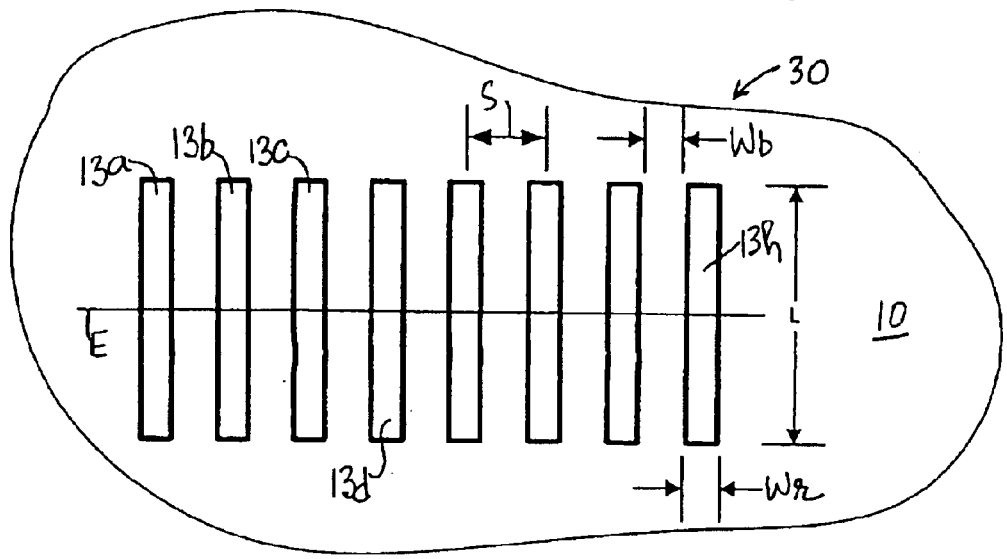
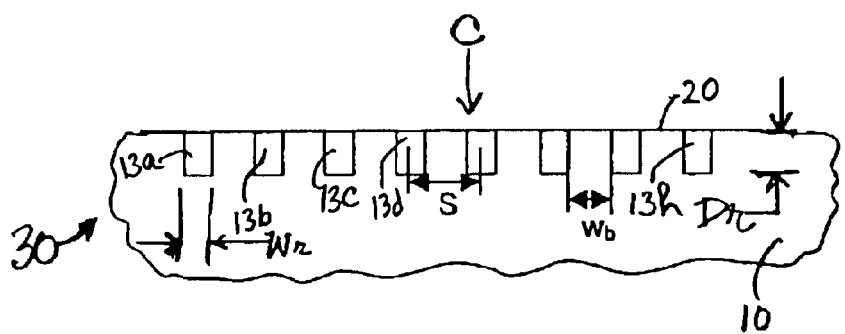
FIG. 4B

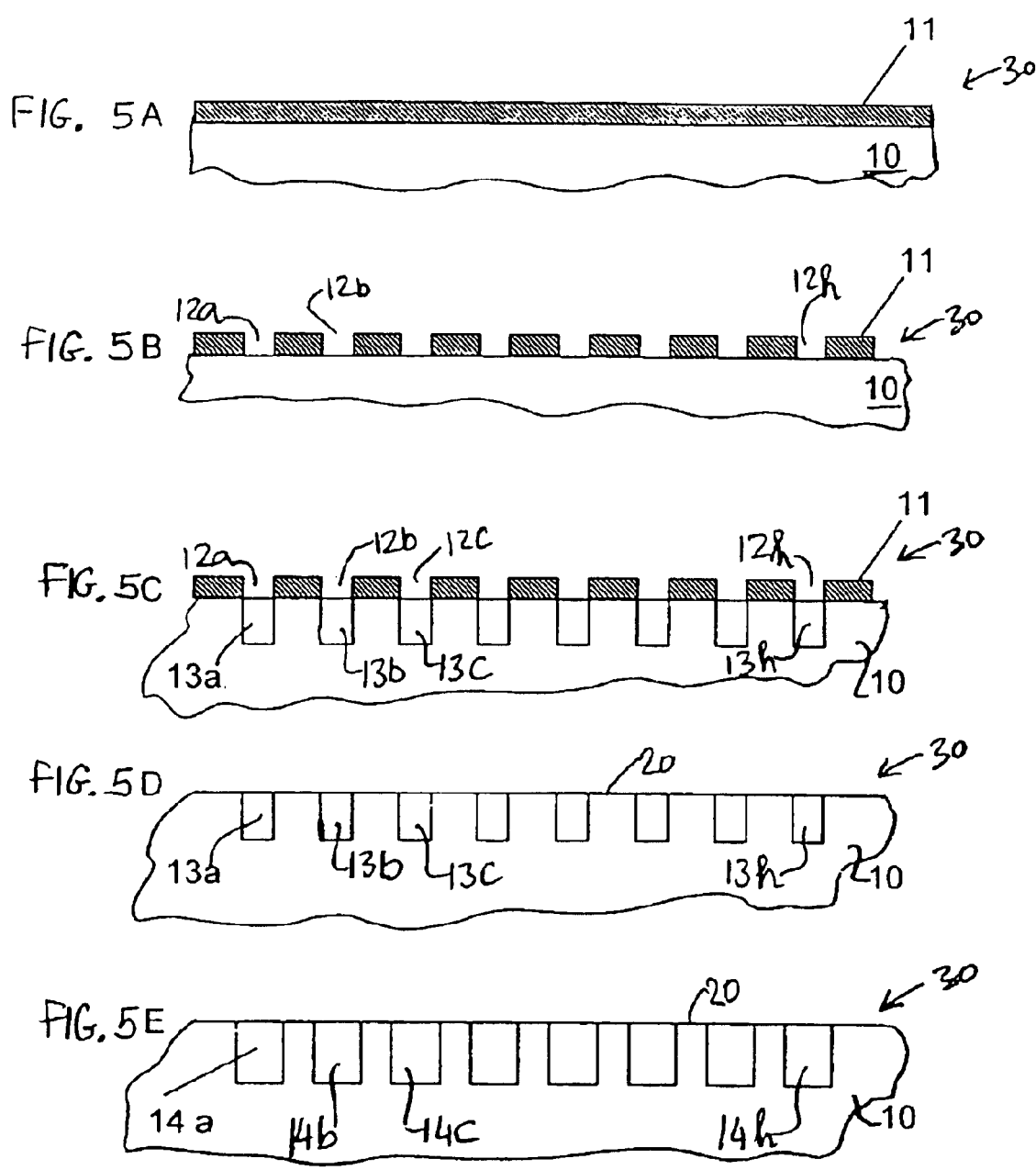

MEASUREMENT OF LATERAL DIFFUSION OF DIFFUSED LAYERS

CROSS-REFERENCE TO RELATED APPLICATIONS

This application is related to and incorporates by reference herein in its entirety, the copending U.S. patent application Ser. No. 09/544,280, filed Apr. 6, 2000, entitled "Apparatus And Method For Evaluating A Semiconductor Wafer" by Peter G. Borden et al., which is a continuation of Ser. No. 09/095,804, filed Jun. 10, 1998 now issued as U.S. Pat. No. 6,049,220.

This application is also related to and incorporates by reference herein in its entirety the U.S. patent application, Ser. No. 09/274,821, filed Mar. 22, 1999, entitled "Apparatus And Method For Determining The Active Dopant Profile In A Semiconductor Wafer," by Peter G. Borden et al., now issued as U.S. Pat. No. 6,323,951.

This application is also related to and incorporates by reference herein in its entirety the copending U.S. patent application, Ser. No. 09/799,481, filed Mar. 5, 2001, entitled "Use of a Coefficient of a Power Curve to Evaluate a Semiconductor Wafer," by Peter G. Borden et al.

FIELD OF THE INVENTION

This invention concerns the measurement of lateral diffusion in the manufacture of small structures such as those used in the source and drain regions of metal-oxide-semiconductor (MOS) transistors in integrated circuits.

BACKGROUND

FIG. 1 shows a cross-sectional view of a MOS field effect transistor (FET) well known in the prior art. Such an MOS transistor typically includes source region 1s and drain region 1d, source extension region 2s and drain extension region 2d, channel 3, gate insulator 4 and gate 5. The source and drain regions 1s and 1d are heavily doped, typically with arsenic for n-type doping or boron for p-type doping. Doping levels are on the order of $10^{20}$ dopant atoms per cubic centimeter. The layers for regions 1s and 1d are typically 500–700 angstroms deep. The extension regions 2s and 2d are also heavily doped, with the same type of dopant atoms as the source and drain regions 1s and 1d, but the extension regions are shallower—typically 300 to 500 angstroms deep. FIGS. 2A and 2B show the doping profiles in the vertical and lateral directions (along the arrows A and B respectively in FIG. 1).

Extension regions 2s and 2d provide contact to the channel region 3. The transistor operates by applying a bias to the gate 5. For example, suppose the regions 1s, 2s, 2d and 1d are n-type, so that the majority carriers are electrons. If a positive voltage is placed on gate 5 with respect to the channel 3, no current will flow between the gate 5 and channel 3 because of the presence of thin gate insulator 4. However, the positive voltage will attract electrons to the gate region 3, creating a thin layer of electrons (called an inversion layer) that connects source extension 2s to drain extension 2d, allowing current to flow between the source and drain. When the voltage on gate 5 is removed, the inversion layer in channel 3 ceases to exist, and the source is disconnected from the drain. In this manner, the transistor can be turned on and off.

In practice, the doping profiles for the various source and drain layers 1s, 1d, 2s and 2d are not perfectly abrupt (box-like). They are usually formed by diffusion processes that may involve several thermal cycles, causing the profiles to be somewhat rounded. For example, FIG. 2A shows two profiles 11a and 11b for the source extension 2s, following arrow A in FIG. 1. Line 11a shows a relatively abrupt profile and line 11b shows a less abrupt profile. Such variation in abruptness (between lines 11a and 11b) may be encountered in different semiconductor wafers under fabrication because each step in the fabrication process has a certain tolerance. Variation in individual process steps or the cumulative variation of a series of process steps can cause a loss of abruptness in the profile (e.g. may go from line 11a to line 11b).

In addition, junction depth may vary depending on process properties, such as, for example, variation in annealing temperature. For example, profile 11b forms a deeper diffused profile than profile 11a.

Similarly, the lateral profile shows a variation in abruptness depending on the tolerance of the individual process steps of semiconductor wafer fabrication. FIG. 2B shows the profile along arrow B in FIG. 1 (arrow B runs parallel to and just underneath the surface of the semiconductor wafer). Profiles 10sa and 10da (FIG. 2B) are more abrupt; profiles 10sb and 10db are less abrupt. In addition, profiles 10sb and 10db have diffused further, reducing the distance between the source and drain regions, and the length of channel 3. The degradation in lateral abruptness due to lateral diffusion is thought to be less severe than the corresponding degradation in vertical abruptness. However, the degradation in lateral abruptness or increase in lateral diffusion can have a greater effect on the performance of the transistor than the vertical abruptness degradation. Lateral and vertical abruptness degradations may also stem from different sources, so that a measure of one is not a measure of the other. For example, stress at the surface may enhance lateral diffusion of dopant atoms, an effect not seen in the vertical direction.

Lateral diffusion and abruptness must be carefully controlled because it directly affects the speed of the transistor and the ability of the transistor to drive the next stage in the circuit. Less lateral abruptness, as with profiles 10sb and 10db (FIG. 2B), causes the portion of the source and drain extensions 2a and 2b (FIG. 1) that contact the channel 3 to have lower doping and, hence, higher resistance. The degradation in lateral abruptness creates a series resistance component that leads to a greater voltage drop between the source 1s and drain 1d (FIG. 1). This voltage drop reduces the ability of the transistor to drive the next stage, reducing the speed of the circuit. Additionally, the lateral distance between the source and drain extensions, 2s and 2d, defines the length of the channel region 3. This channel length directly determines certain properties of the transistor, such as cutoff frequency.

Some of the prior art methods for measuring lateral diffusion (identified by how far the junction moves laterally during anneal) and abruptness (which is defined by the slope of the diffused profile) are electrical probing of transistors, capacitance atomic force microscopy (C-AFM), and inference from vertical secondary ion mass spectroscopy (SIMS) profiles.

Inference of lateral diffusion and abruptness is possible from electrical probing of transistors. This procedure requires contact to a full transistor structure. Consequently, electrical probing is impractical at the point in the process when the doped layers are being formed and the transistor is still incomplete. The time between the source/drain process steps and the first opportunity to probe can be days or weeks, greatly reducing the ability to implement real-time process control.

Probe methods such as C-AFM require sectioning of the transistor and various intermediate preparation steps. Even when this is complete, probing requires several hours, and the resolution is typically worse than 100 Å, too poor to provide an accurate measure of diffusion or abruptness for purposes of process control.

It is also possible to infer the lateral diffusion and abruptness from the vertical profile (of the type shown in FIG. 2A), assuming the lateral and vertical diffusion and abruptness relate to the same physical phenomena. However, methods such as SIMS are slow and destructive, and therefore not suited for routine in-line process control. In addition, as mentioned above, there may be certain cases where the lateral and vertical diffusion and abruptness do not fully relate to one another.

SUMMARY

Any semiconductor wafer fabrication process may be changed, in accordance with the invention, to monitor lateral diffusion and abruptness of doped layers as a step in the wafer fabrication process (or alternatively during development of such a process). In some embodiments, such monitoring is used to control one or more parameters in the wafer fabrication process, e.g. to improve yield of the process.

Specifically, in one embodiment, a test structure including one or more doped regions is formed in the semiconductor wafer (e.g. simultaneously with one or more transistors) and one or more dimension(s) of the test structure are measured, and used as an estimate of lateral diffusion and abruptness in other doped regions in the wafer, e.g. in the simultaneously formed transistors.

Test structures of the type described above can be small—e.g. a few microns on a side—and can be placed at predetermined locations on a production wafer. Doped regions in test structures can be located at regularly spaced intervals relative to one another, or alternatively may be located with varying spacings-between adjacent doped regions.

Alternatively or in addition, multiple test structures may be formed in a single wafer, with doped regions at regular spatial intervals in each test structure, while different test structures have different spatial intervals.

In another embodiment, fully doped and undoped regions are included in the test structure. These are used to calibrate effects of junction depth variation. In another embodiment, a measurement of photoresist linewidth is included in order to calibrate out the effect of linewidth errors due to variation in the lithographic process.

In yet another embodiment, in certain cases doped line and space structures are available as part of the pattern of the chip. For example, resistors are doped lines. In these cases, measurements are made directly in the active area of the integrated circuit, without the need for test structures.

In one embodiment, one or more test structures of the type described above are monitored immediately after formation of doped layers, so as to implement real-time control of a wafer fabrication process. However, such evaluation of device properties may also be performed off-line (e.g. with non-production wafers), and used for process development in alternative embodiments.

BRIEF DESCRIPTION OF THE DRAWINGS

FIGS. 4A and 4B illustrate, in a plan view and a cross-sectional view respectively, a test structure for estimating lateral diffusion of doped regions of a transistor, in one embodiment of the invention.

FIGS. 5A–5E illustrate, in a series of cross-sectional diagrams, a process of creating a test structure of the type illustrated in FIGS. 4C and 4D.

Note that these drawings are not to scale.

DETAILED DESCRIPTION

One embodiment of this invention is based on the creation of a test structure in a semiconductor wafer and subsequent non-contact measurement of one or more properties of the test structure. Measurement of such test structure properties may be used, for example, to estimate lateral diffusion in doped regions in a transistor, e.g. if the test structure also-includes doped regions.

In some embodiments, such measurements are used to control the wafer fabrication process, in a feedback loop. Specifically, in one embodiment, one or more test structures are formed in a production wafer, e.g. simultaneous with transistor fabrication, as illustrated in act 301 (FIG. 3A) If lateral diffusion of doped regions of a transistor is to be estimated, the test structure formed in act 301 may require implantation of dopant atoms, and depending on the embodiment such implantation may be performed simultaneously with implantation for formation of transistors of the wafer. Note however that in alternative embodiments, other kinds of test structures may be formed, e.g. by formation of a portion of a metallic layer if a property of a metallic layer is to be estimated.

Figure 1:
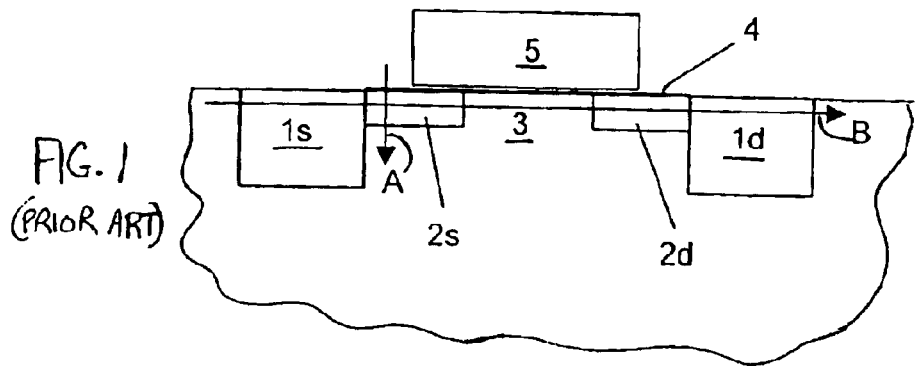
FIG. 1 shows, in a cross-sectional diagram through a prior art semiconductor wafer, the structure of a MOS field effect transistor.
Figure 2A:
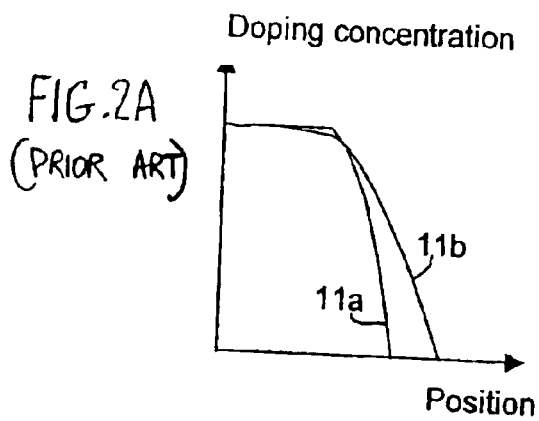
FIGS. 2A and 2B show, in graphs, the doping profile of the prior art semiconductor wafer, along arrow A of FIG. 1 through extension layer 2s, and along arrow B of FIG. 1 through the transistor and parallel to the wafer surface respectively.
Figure 2B:
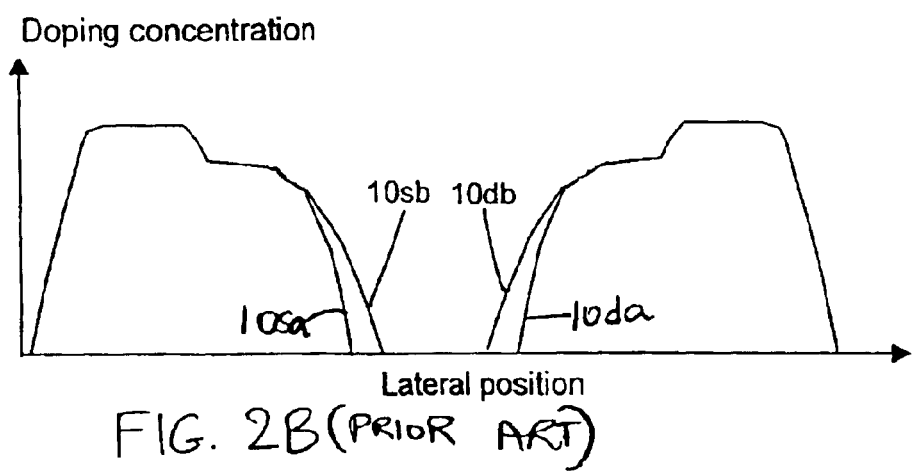
Figure 3A:
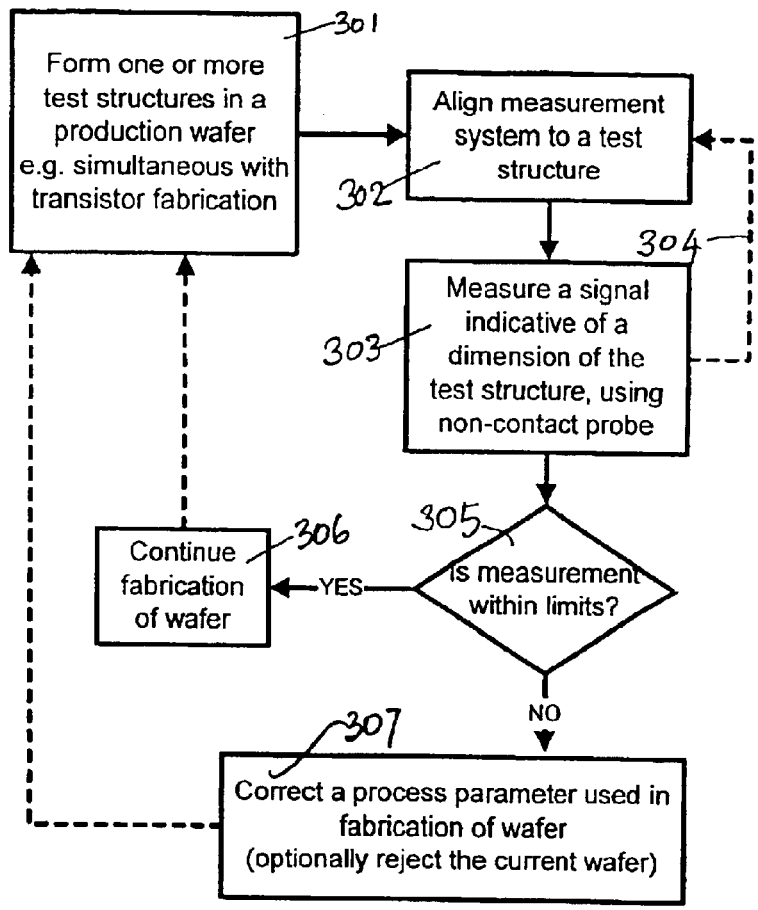
FIG. 3A illustrates, in a decision chart, use of a measurement of a dimension of test structure, to decide whether a process is in control, in accordance with the invention.

Once one or more test structures are formed, a wafer containing the test structures is aligned to a measurement system (see act 302 in FIG. 3A), followed by measurement of a signal indicative of a dimension of the test structure, using a noncontact probe (see act 303 in FIG. 3A). One or more of acts 302 and 303 may be repeatedly performed, e.g. for multiple test structures as illustrated by act 304, and may be interleaved with or performed simultaneously with other kinds of measurements as would be apparent to the skilled artisan.

Thereafter, the measurements performed in act 303 are compared with predetermined control limits, and if the measurements fall within the limits, fabrication of the wafer is continued (see act 306 in FIG. 3A), followed by returning to act 301 (described above) to form additional test structures in the same wafer, or in another wafer. If the measurement falls outside the predetermined control limits, a process parameter that is used in fabrication of the wafer is changed (see act 307 in FIG. 3A), and depending on the deviation the current wafer may be rejected or alternatively may be processed further.

Figure 3B:
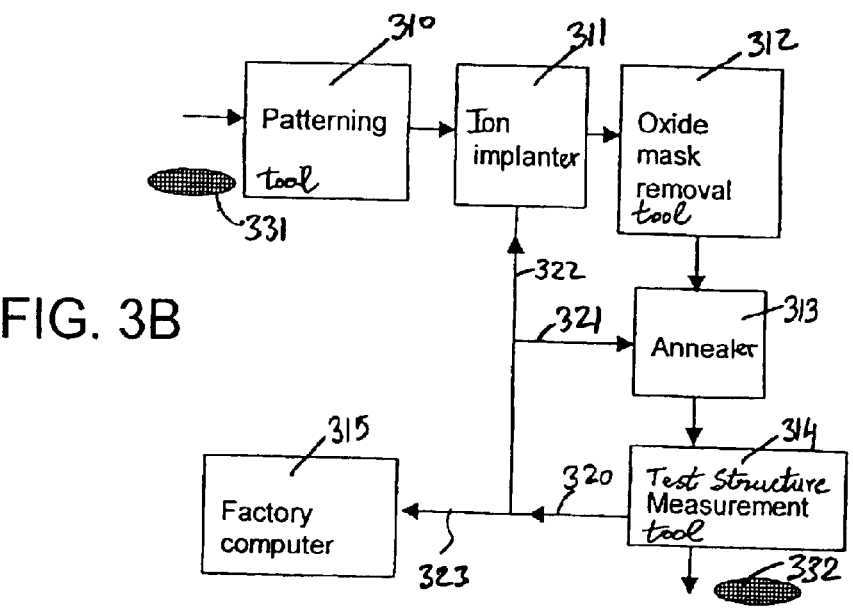
FIG. 3B illustrates, in a block diagram, use of a test structure measurement tool in-situ, with other wafer fabrication tools, in accordance with the invention.

Therefore, measurement of the test structure's properties is performed in an in-situ manner during fabrication of a wafer and in one embodiment, a measurement tool 314 (FIG. 3B) is co-located with other wafer fabrication tools, such as an annealer 313, an ion implanter 311, a patterning tool 310 and an oxide mask removal tool 312. A wafer 331 (FIG. 3B) may enter a patterning tool 310, wherein patterns associated with the source and drain extensions of to-be-formed transistors, and also doped regions of one or more test structures are formed on wafer 331.

In one embodiment, after patterning and before ion implantation, width of the patterned lines is measured using a commonly available tool, such as a scanning electron microscope (SEM). The linewidth measurement in this embodiment is used to correct for errors in lithographic patterning that can affect the to-be-performed analysis of the lateral diffusion measurement.

Thereafter, wafer 331 is inserted into an ion implanter 311 wherein dopant atoms are implanted. Next, an implant mask is removed by tool 312, and the wafer is annealed in an annealer 313. Thereafter, test structures in the wafer are evaluated by tool 314 as described above in reference to acts 302–303. The measurement signal generated by tool 314 may be supplied on a bus 320 that is connected via connection 321 to annealer 313 and via connection 322 to ion implanter 311, thereby to provide feedback signals to these tools 311 and 313. Alternatively, or additionally, the measurement signals on bus 320 may be provided via connection 322 to a factory computer 315. Factory computer 315 may archive the measurement signals for later correlation to electrical performance of the devices on wafer 331, for example.

Any one of a number of methods well known in the art may be used in performance of act 303 (FIG. 3A) to measure dimensions, or other properties of a test structure formed in a production wafer in accordance with the invention. For example, one or more methods of the type described in U.S. patent applications, Ser. Nos. 09/544,280, 09/274,821, and 09/799,481 (incorporated by reference above) may be used in the manner described above in reference to FIGS. 3A and 3B. Moreover, depending on the specific application, any kinds of test structures may be formed within production wafers, as would be apparent to a skilled artisan in view of the disclosure.

FIGS. 4A and 4B show in plan and cross-sectional views one example of such a test structure. In the example of FIG. 4A, the test structure includes a number of ion implanted regions 13a–13h (eight regions are shown by way of example, although more or less may be used depending on other considerations, such as the ability of the measurement system to align to a pattern, or space limitations within the integrated circuit die).

Regions 13a–13h of the test structure in the wafer may be each identical in dimension (e.g. rectangular boxes), and oriented parallel to one another, so that they form an array of parallel line segments 13a–13h (FIG. 4A) when viewed in the direction C from above the wafer 30 (FIG. 4B). In this example, regions 13a–13h are each oriented perpendicular to a common straight line E (FIG. 4A), so that these implanted regions are parallel to one another.

In one specific embodiment, implanted regions 13a–13h have center-to-center spacing S and inter-region distance $w_b$. When designing the test structure containing regions 13a–13h, one may plan to minimize the pitch (S) within the constraint of the resolution of the available lithography. This increases the effect on the measured signal of small changes in dimensions e.g. due to lateral diffusion. For example, S could be chosen to be 0.26 μm and $w_b$ could 0.13 μm depending on the geometry of the lithography. Although in the embodiment illustrated in FIG. 4A each of S and $w_b$ are identical between any two of the regions 13a–13h that are adjacent to one another, in alternative embodiments other predetermined geometries may be used. For example, in one alternative embodiment, the distances S and $w_b$ progressively increase in predetermined direction, e.g. from left to right along the line E. Moreover, in another embodiment, a number of such test structures are formed, and although the distances S and $w_b$ are the same within a test structure, these distances are different for different test structures.

Furthermore, in the example illustrated in FIGS. 4A and 4B, the width $w_r$ of each of regions 13a–13h is identical to the inter-region distance $w_b$, for example 0.13 μms. However, the method of FIG. 3A works equally well if $w_r$ is not equal to $w_b$ in this example. Note that there is no constraint between the width of the bars and the width of the spaces when using the method of FIG. 3A. The method works equally well if the bar and space widths are different.

As noted above, one may plan to make the dimensions of a test structure as small as possible. This plan allows measurement of the extent to which the lateral diffusion closes off space $w_b$. The effect is proportional to the fraction $2d/w_b$, where d is the lateral diffusion distance (the factor of 2 arises because the diffusion is happening from both sides). For example, if the lateral diffusion is d=0.03 μm and $w_b$ is 0.13 μm, then the fractional effect is 0.06/0.13, or about 50%. If $w_b$ is larger, say 1 μm, then the effect is only 0.06/1, or about 6%. Thus, one may plan to make the dimensions as small as possible. Also, the width of the doped region $w_R$ may be selected to be at least double the lateral diffusion, so that the dopant in the doped bars does not get depleted by lateral diffusion.

In the embodiment that uses progressively increasing spacing S between adjacent regions 13a–13h, could be increased from 0.26 to 0.5 μm with constant pitch (equal bar and gap). Alternatively, S could be increased from 0.26 to 0.5 μm with constant gap of 0.13 μm and varying doped bar length, or constant doped bar width of 0.13 μm and varying gap.

In one embodiment, an ion implant used to form regions 13a–13h (FIG. 4A) has exactly the same energy and dose as the ion implant used to form source/drain extension regions of a transistor that is present (as a part of the normal circuitry) in the semiconductor wafer. The energy and dosage for a test structure may be selected to be the same as the MOS transistor for two reasons: first, it best represents the real transistor doping and second it requires no additional process steps. In the embodiment of illustrated in FIGS. 4A and 4B, the dopant atoms are implanted up to a depth of Dr (FIG. 4B), which can be, for example, 50 Å. These implants may be made very shallow, typically <100 Å In this embodiment, the implant parameters are the implant specie (B, As, P, Sb, etc), the energy (0.2 to 2 keV typically), and the dose ($1 \times 10^{14}$ to $3 \times 10^{15}$ atoms/cm$^2$ typically). The anneal parameters are typically the temperature (on order of 1000° C.), time (instant to 10 sec), ramp-up rate (50 to 200° C./sec) to temperature and ramp-down time (same as ramp-up rate).

The length (FIG. 4A) of the implanted regions 13a–13h (in a direction perpendicular to the plane of the paper in FIG. 4B) is typically several microns (on the order of or greater than 10 microns), to allow alignment of a laser spot (used during measurement as discussed below) with the test structure. Therefore, line length L of about 10 μm can be smaller in the future if a currently possible spot size of 3 μm (described below) is made proportionally smaller. The resolution of such a method is currently less than 10 Å in one embodiment.

Figure 4C:
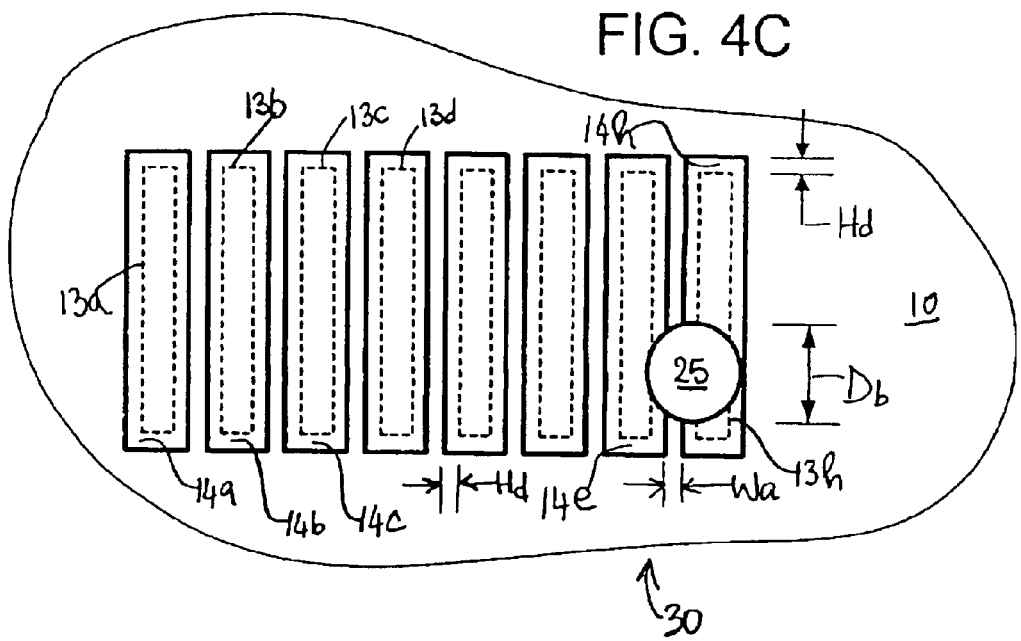
FIGS. 4C and 4D illustrate, in a plan view and a cross-sectional view respectively, the test structure of FIGS. 4A and 4B after removal of oxide mask 11 and annealing.

Following anneal of wafer 30, the size of the implanted regions increases due to diffusion, as shown in FIG. 4C. The originally formed regions 13a–13h in wafer 30 are shown with dashed lines and after anneal have become larger and are labeled as regions 14a–14h. Regions 14a–14h (FIGS. 4C and 4D) now have an inter-region spacing $w_a$, where $w_a < w_b$. Exemplary values are $w_b$=200 nm; $w_a$=120 nm.

A process for making a test structure of the type described above in reference to FIGS. 4A and 4B is illustrated in FIGS. 5A–5D, for one embodiment. First, photoresist layer 11 is applied to the surface of wafer 30 (FIG. 5A). Next, photoresist layer 11 is patterned by exposing and developing the resist, creating holes 12a–12h, in photoresist layer 11 (FIG. 5B).

The just-described acts (in the previous paragraph) may also be used simultaneously for the creation of one or more portions of a transistor in the silicon wafer. For example, the source and drain regions, and extensions thereof may be formed simultaneously with formation of regions 13a–13h, depending on the embodiment. If so, layer 11 has holes at the locations of the to-be-formed regions of the transistors, in addition to the holes 12a–12h required for forming the test structure. Alternatively, all of the regions of the various transistors in wafer 30 may be formed by acts separate and different from the just-described acts, again depending on the embodiment.

Ion implantation is applied, to form regions 13a–13h beneath holes 12a–12h (and beneath any additional holes that may be present for the formation of transistors as noted above). Photoresist layer 11 blocks the ion implant elsewhere (FIG. 5C). Photoresist 11 is then removed, leaving implanted regions 13a–13h in substrate 10 (FIG. 5D).

Note that the width of patterned regions 13a–13h may not be equal to the width as seen on the mask used for the lithographic patterning. For example, if the pattern is overexposed, the lines may be widened. In some embodiments, knowledge of linewidth is used to extract a measure of lateral diffusion. In such cases, a measurement of the actual linewidth using an SEM is performed at this point in some embodiments of the process.

Finally, the wafer is annealed, causing diffusion of the implanted regions 13a–13h, resulting in expanded doped regions 14a–14h (FIG. 5E). The expanded doped regions 14a–14h are deeper than the corresponding implanted regions 13a–13h by a distance Vd, and are also larger in the horizontal dimension by a distance Hd. The change in horizontal dimension Hd is related to a corresponding in the vertical dimension Vd by the following rule of thumb: the lateral diffusion is about 0.7 times the vertical. A method of the type described herein eliminates the need to rely on such a rule of thumb because the lateral diffusion is actually measured. As noted above, such steps may be carried out in conjunction with transistor fabrication steps, such as etching of contact holes or gate structures. Thus, no additional masking or process steps may be required for test structure formation beyond those normally used to form the integrated circuit, i.e. normally needed even in the absence of the test structure.

Lateral diffusion during anneal across the distance Hd causes reduction in the spacing $w_b$ between doped regions 14a–14h (also called "doped fingers"). Therefore, measurement of spacing reduction $w_a$–$w_b$, in one embodiment of the invention, provides a measurement of the lateral diffusion between the source and drain extensions 2s and 2d. This spacing reduction measurement may be performed by measuring the distance $w_b$ and $w_a$ before and after anneal, e.g. as described below in reference to FIG. 6. The distance before anneal $W_b$ is equal to the width of the printed mask in one example, and can be measured using an SEM; the distance after anneal $W_a$ is measured using a method described here. However, as noted above, other methods may be used to measure such spacings. And in certain embodiments, instead of computing the spacing reduction $w_a$–$w_b$, either spacing $w_a$ or spacing $w_b$ or both are individually used to implement process control.

To measure the spacing $w_a$ or $w_b$ between doped regions, one or more beams of light may be shone on the test structure, depending on the embodiments. Specifically, a first beam of light (also called "pump beam"), with photons above the bandgap energy of the semiconductor material, is initially focused on the test structure (as illustrated by act 601 in FIG. 6). Excess carriers (electrons and holes) are generated when the test structure is so illuminated, and the excess carrier concentration is high in the lower doped regions, and low in the higher doped implanted regions. In addition, a second beam (also called "probe beam") is used for measurement (as per act 602 in FIG. 6), and in FIG. 7A both beams (which are coincident) are represented by the arrow 16 which is also labeled $P_{IN}$. The difference in carrier concentrations results in a higher carrier distribution in cross-hatched region 15 (see FIG. 7A) than in the doped regions 14a–14h.

Figure 7A:
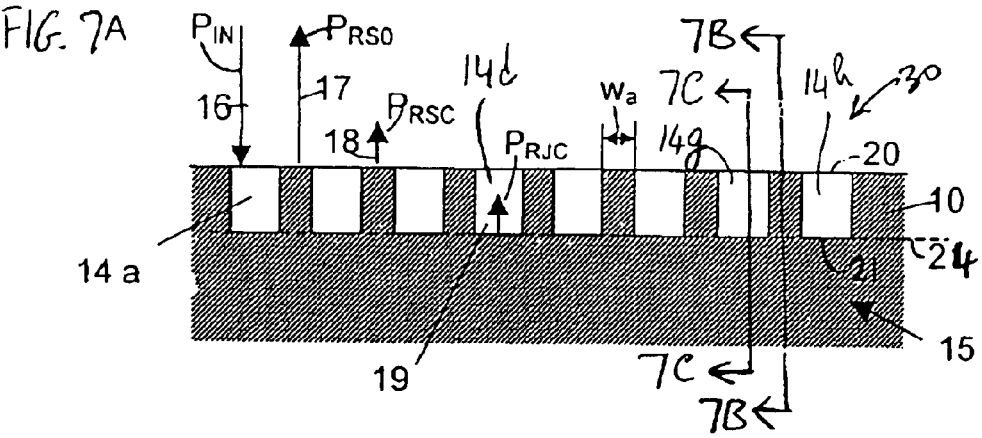
FIG. 7A shows, in a cross-sectional diagram, the test structure of FIGS. 4A and 4B under illumination, and illustrates reflection components from the surface carrier distribution, and from the depth carrier distribution.
Figure 7B:
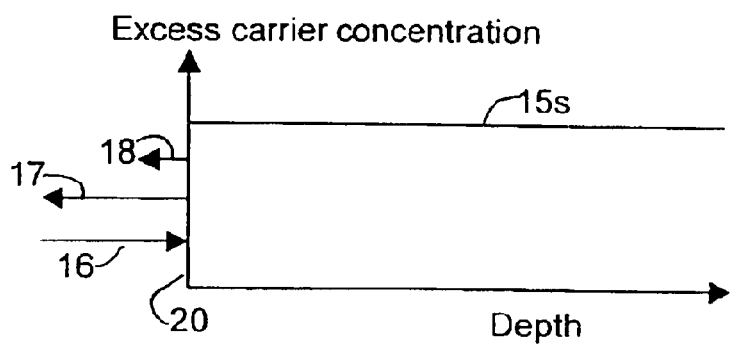
FIG. 7B shows, in a graph, excess carrier concentration as a function of depth along a centerline between adjacent doped regions $14b$ and $14c$, as measured by a surface reflection component $P_{RSC}$.
Figure 7C:
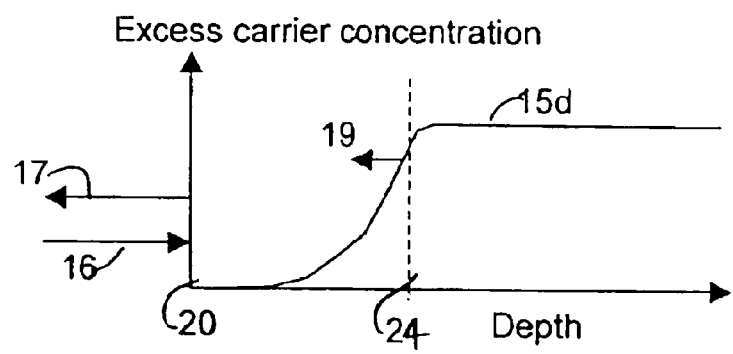
FIG. 7C shows, in a graph, excess carrier concentration as a function of depth along the centerline of a doped region $14d$, as measured by a depth reflection component $P_{RJC}$.

FIGS. 7B and 7C show the excess carrier concentration as a function of depth. These graphs show the excess carrier concentration due to illumination by the pump beam; that is, the carrier concentration that varies at the modulation frequency of the generation beam (and not the total carrier concentration which is normally higher due to presence of background carriers).

In the areas between doped regions 14a–14h, the excess carrier concentration 15s (FIG. 7B) remains approximately constant (FIG. 7B) all the way from surface 20 up to the end of the doped region in substrate 10. The depth of the doped region might be on the order of 200 to 400 Å. The concentration stays approximately constant to a much greater depth—several microns. The value of the carrier concentration 15s depends on the intensity of the pump beam. For illumination levels on the order of 5 mW of laser power at the wafer surface 20, with a beam of wavelength of 830 nm focused into a spot of 3 μm diameter, the excess carrier concentration 15s may be on the order of $1 \times 10^{18}$ carriers/ $cm^3$ within the beam diameter, i.e. the illuminated region. The excess carrier concentration tapers off outside the beam. However, what happens outside the generation beam diameter is immaterial to the measurement method as long as the probe beam spot is within the spot of the pump.

Along a vertical line drawn through a doped region 14d, the excess carrier concentration 15d (FIG. 7C) increases as the distance from the surface 20 is increased. Doped region 14d is identical to regions 14a–14h. For this reason the same profile (FIG. 7C) is also seen at a vertical cut line 7C—7C through doped region 14g in FIG. 7A. The excess carrier concentration 15d is the concentration profile along a cut line through any of doped segments 14a–14h. A second cut line 7B—7B through the gap between two doped segments 14g and 14h has an excess carrier profile in FIG. 7B along that cut line.

At locations below each of the doped regions 14a–14h, typically, a few hundred (200–300) Å below boundary 21 the concentration 15d (FIG. 7C) becomes approximately equal to the concentration 15s (FIG. 7B). However, when going vertically upwards along the vertical line from substrate 10 towards wafer surface 20, the concentration 15d is initially constant until a horizontal boundary 21 of doped region 14d, and at this boundary 21 the concentration 15d drops rapidly, and may be several orders of magnitude lower than the concentration 15s. In FIG. 7A, a dashed line 24 indicates the plane in which boundary 21 is present for each doped region.

Figure 10:
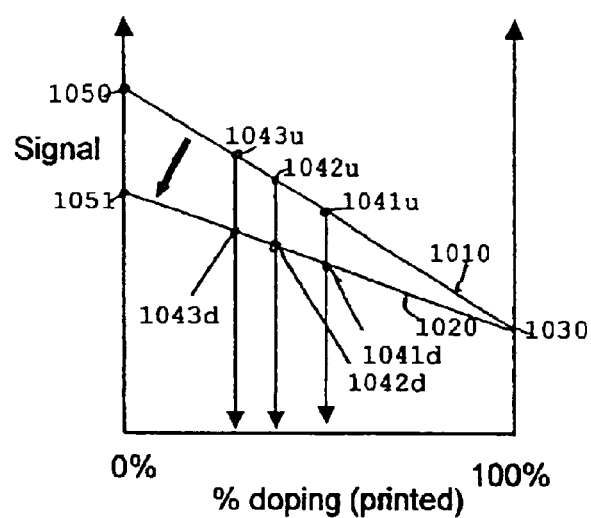
FIG. 10 illustrates, in a graph, extracting lateral diffusion from the slope of a line (which shows a loss of the measured signal with increase in doping).

Horizontal abruptness measurement may be determined as described below because the net signal is (% of area in gap)×signal from surface+(% of area in doped region)× signal from junction 24). As the lateral diffusion increases, the percentage of area in doped region increases and percentage of area in undoped region decreases. Therefore, the measured signal is a measure of lateral diffusion. Also, the measured signal is a function of junction depth 24, so that junction depth is part of the measurement, and junction depth may be extracted as shown in FIG. 10 and discussed below.

The index of refraction of silicon is a well known function of its conductivity, and increases linearly with the excess carrier concentration according to the relation $$\Delta n = \frac{q^2 N}{2\varepsilon_0 \varepsilon_1 m^* \omega^2} \quad (1)$$

where Δn is the change in the index of refraction, N is the excess carrier concentration (in the present case, the difference between the concentration in the dark and the concentration under conditions of carrier generation such as by illumination), $\varepsilon_0$ is the permittivity of free space, $\varepsilon_s$ is the dielectric constant of silicon, m* is the carrier effective mass, q is the electron charge, and ω is the frequency of the light illuminating the carriers. This relationship results from the well-known Drude model of conduction (see Jackson, Electrodynamics).

As a consequence of the index of refraction change induced by the excess carrier concentration, a sharp gradient in the index of refraction arises at the wafer surface 20 between the doped regions, and a lesser gradient arises at the lower boundary 21 of the diffused regions 14a–14h. However, the surface gradient is much smaller in the doped region (because of the smaller excess carrier concentration in the doped regions). Also, the gradient at depth 24 is not present in the gaps between doped regions 14a–14h because there is no doping step at that depth in the gap regions.

Probe beam 16 (FIG. 7A) may be polarized along the length of diffused regions 14a–14h (i.e. polarized along a line perpendicular to the plane of the paper in FIG. 7A), although the probe beam 16 may also be unpolarized depending on the embodiment. Polarization of either or both of the pump and probe beams parallel to the length increases sensitivity to the presence of the doped regions and spaces between those regions, as described in the U.S. patent application Ser. No. 09/521,232 filed Mar. 8, 2000, Attorney Docket No. [M-7850]. Various reflection components arise when the probe beam is incident on the semiconductor wafer 30, and are shown in FIG. 7A as arrows 17, 18 and 19. Reflection component 17 arises from the front surface 20 due to the change in materials from air to silicon. This reflection component 17 of the probe beam is present whether or not excess carrier distribution 15 exists. Another reflection component 18 also comes from the surface 20, and is due to the index of refraction component introduced by the sharp gradient in excess carrier concentration 15s at the surface 20 of semiconductor 10. Yet another reflection component 19 is due to the gradient in excess carrier concentration 15d at the lower edge 21 of the doped regions 14a–14h.

Figure 6:
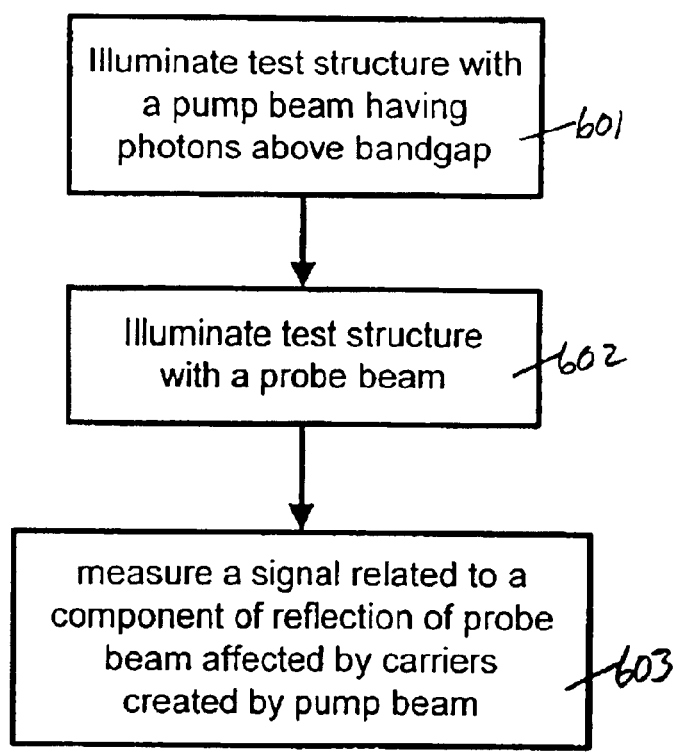
FIG. 6 shows, in a flow chart, the process of measurement.

One embodiment includes modulating the first light beam, and measuring the intensity of a modulated component of the reflection of the second light beam with a lock-in amplifier, e.g. as illustrated by act 603 (FIG. 6). However, because components 18 and 19 are present only when the excess carriers are present, these components may be distinguished from other reflections if the carrier generation (e.g. by the first light beam) is turned on and off. Reflection of the second light beam may be therefore measured with first light beam turned on, and then again with the first light beam turned off, and a difference may be taken between these two measurements, to implement act 603.

If the intensity of the first light beam is modulated, the modulation frequency is in one embodiment lower than the inverse of the carrier lifetime in the undoped region. This is used in certain embodiments to allow the carrier distribution described in FIG. 7C to form. For a lifetime of 100 microseconds, the frequency may be chosen to be under 10 kHz, and could be different in other embodiments. A signal that can be measured will be present at higher frequencies, but may be degraded. One preferred embodiment, therefore, uses the lower frequency. At higher frequencies, carrier waves will also be generated. In this case, the carrier concentration distribution described above, which is a consequence of a solution to the static diffusion equation, will not be met, and the signal will result from a superposition of reflections from carrier waves and a static distribution, the latter of which provides the signal of interest.

Specifically, the time dependent diffusion equation under the condition of periodic excitation at a frequency ω is $$\frac{\partial^2 n}{\partial z^2} - \frac{n}{D}\left(\frac{1}{\tau} - j\omega\right) = 0 \quad (2)$$

where D is the diffusivity, τ is the lifetime, n is the excess carrier concentration, and j is the square root of (−1). When $\omega \gg 1/\tau$, then the second term is imaginary and a wave solution results. Conversely, when $\omega \ll 1/\tau$ a static solution results.

Note that the relative intensity of component 18 arising from the surface concentration of excess carriers is a function of the lateral diffusion. Consider, for example, the extreme case where lateral diffusion has completely eliminated the spaces between the diffused regions ($w_a=0$). In this case, component 18 is zero. In the opposite case of zero lateral diffusion, component 18 is a maximum. Thus, component 18 will vary monotonically with the lateral diffusion, and a measurement of its intensity relates to the lateral diffusion.

The signal at a detector may be described in terms of reflection components 17, 18 and 19 as follows. The reflection amplitude from surface 20 is the sum of components 17 and 18, written as $$r_s = r_{s0} + \Delta r_s \quad (3)$$

where the first term on the right hand side is component 17 and the second term is component 18. Component 19, the reflection amplitude from the lower side 21 of the diffused region, is phase shifted by the transit of the light to the lower side 21 and back, and is written as $$r_j(z) = r_j e^{j2nkz} \quad (4)$$

where n is the index of refraction of silicon, $k=2\pi/\lambda$ is the wavenumber, where $\lambda$ is the wavelength, and z is the distance between surface 20 and lower side of the diffused region 21.

The power at the detector is the squared magnitude of the sum of the reflections, given by $$P = |r_{s0} + \Delta r_s + r_j e^{j2nkz}|^2 = r_{s0}^2 + 2r_{s0}\Delta r_s + 2r_{s0}r_j \cos(2nkz) \quad (5)$$

In the above expression, terms of second order have been dropped, since the reflection component $r_{s0}$ is typically several orders of magnitude larger than the other terms. If the signal is filtered to remove the dc component, only the last two terms remain, $$P = 2r_{s0}(\Delta r_s + r_j \cos(2nkz)) \quad (6)$$

Note that there are two terms in the parenthesis. The relative magnitude of the two corresponds to the relative width of the doped regions and undoped regions at the wafer surface. In addition, the second term is a function of the vertical depth of the doped regions.

From the above equation, it is seen that the measured signal is a linear superposition of signals from the doped and undoped regions. In one extreme, the wafer is undoped (doped region width is zero), and the signal is that obtained from an undoped wafer. In the other extreme, the wafer is fully doped (undoped region—gaps between doped lines—width is zero) and the signal is that obtained from a doped wafer. The signal varies linearly between these extremes as a function of the ratio of the surface area that is doped to the area that is undoped.

Figure 7D:
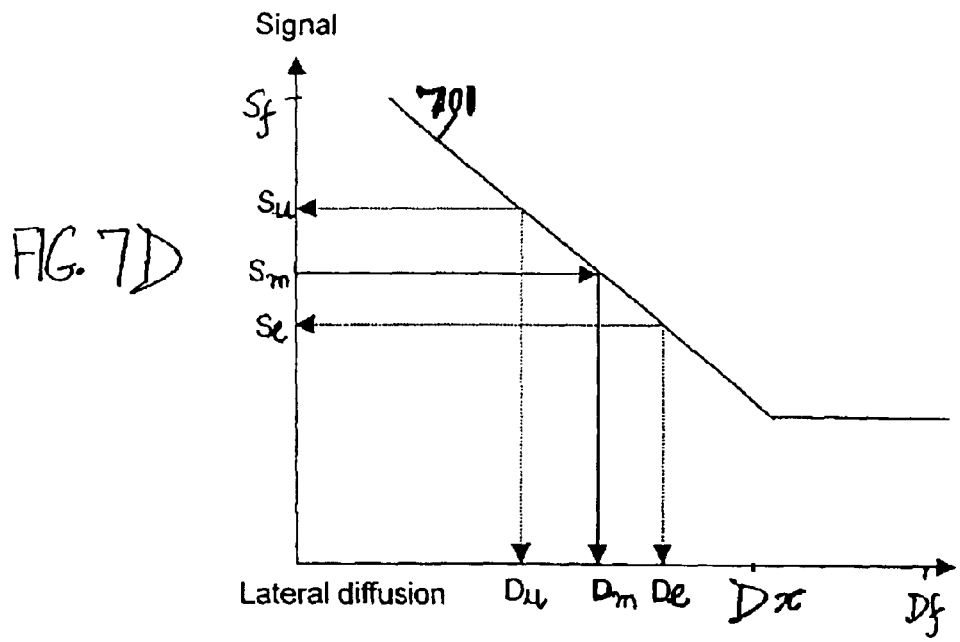
FIG. 7D illustrates, in a graph, a calibration plot of the measured signal as a function of lateral diffusion from reference wafers, showing how a measurement is converted into a lateral diffusion value and how control limits are set for a process.

Lateral abruptness is found in one embodiment using the graph shown in FIG. 7D. Response curve 701 is found using separate calibration experiments on reference wafers that may be tested using a prior art method. In these experiments, samples of the test structures are made in reference wafers and annealed for successively longer periods of time or temperature. The samples are measured as described above in reference to FIG. 6 to provide a signal. The depth Dr (FIG. 4B) of the annealed diffused regions may be found using a conventional method such as SIMS (which provides an estimate of the amount of diffusion).

In one example, the curve 701 is defined by the values in the following table:

| Symbol in FIG. 7D | Value |
|---|---|
| Sf | 20,000 μV/Conditioned |
| Sl | 17,600 μV/Conditioned |
| Sm | 18,000 μV/Conditioned |
| Su | 18,500 μV/Conditioned |
| Df | 500 Å |
| Du | 200 Å |
| Dm | 250 Å |
| Dl | 300 Å |

In the example illustrated in FIG. 7D, the test structure was formed by doped lines 2800 Å wide and the spacing between lines was 2400 Å. The signal that was measured was for a junction depth of 400 Å.

Figure 4D:
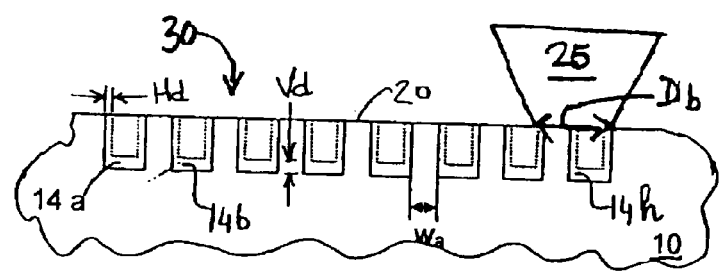

As seen in FIG. 7D, after the sloped region of curve 701 there is a flat region for the following reason. In some reference wafers that have the largest annealing time and/or temperature the diffusion completely connects the diffused regions, causing spacing $w_a$ to be zero and curve 701 to flatten, as shown for large amounts of lateral diffusion greater than Dx (FIG. 4D). Therefore the location of point Dx provides a measure of the ratio of lateral diffusion Hd to vertical diffusion Vd (FIG. 4D), since it occurs when the amount of lateral diffusion Hd equals half the space $w_b$ between the implant regions, that distance $w_b$ being set by the mask pattern.

This calibration curve 701 (FIG. 7D) can then be used to control a diffusion process in a wafer under fabrication (also called "production wafer"). An unknown sample is measured as described above in reference to FIG. 6 and found to have a signal $S_M$. This signal corresponds to an amount of lateral diffusion $D_M$, as determined from curve 701. Upper and lower signal control limits $S_U$ and $S_L$ can be set, corresponding to maximum and minimum amounts of lateral diffusion $D_U$ and $D_L$. When the measured signal exceeds these limits $S_U$ or $S_L$, an alarm can be set and/or adjustments made automatically.

Figure 8:
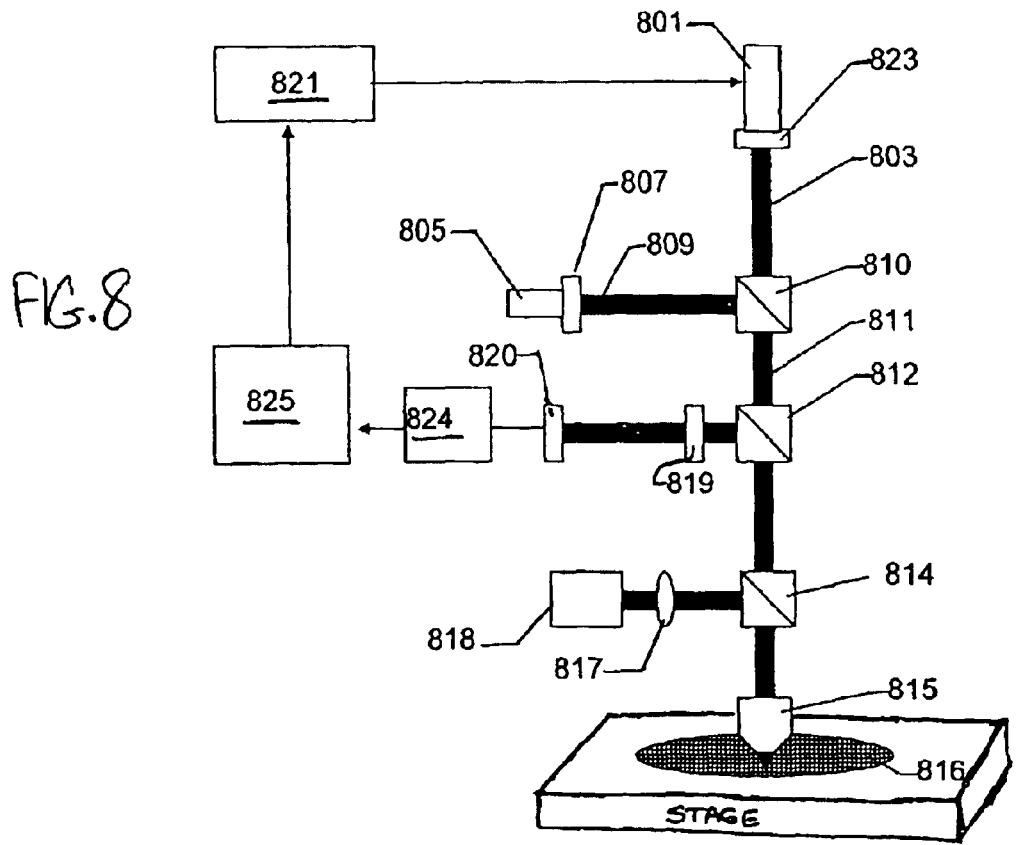
FIG. 8 illustrates, in a block diagram, the hardware configuration for evaluation of a test structure in the manner illustrated in FIG. 6.

The preferred hardware configuration is shown in FIG. 8. Carrier generation laser 801 is a diode pumped laser with a wavelength of 830 nm (Spectra Diode Labs, San Jose Calif.). Its output is collimated with collimating lens 823, providing collimated beam 803. Measurement laser 805 is a diode pumped laser with a wavelength of 980 nm (Spectra Diode Labs, San Jose, Calif.). Its output is collimated with collimating lens 807, providing collimated beam 809.

Beams 809 and 803 are combined using dichroic mirror 810 to create combined beam 811. This beam passes through 50:50 beam splitter 812, 90:10 beam splitter 814, and objective lens 815 (100X, Olympus, Tokyo, Japan). Lens 815 focuses beam 811 onto the surface of wafer 816. The reflected signal components are recollimated with lens 815. Beam splitter 814 diverts 10% of the return beam to lens 817 and camera 818, which provide a system to align the beam spot to the pattern.

Not shown in FIG. 8 is an autofocus system that includes a pinhole and detector, which also uses the portion of the return beam diverted by beam splitter 814. The return beam then enters beam splitter 812, which passes it through optical filter 819. Filter 819 passes the light from measurement laser 805, but blocks light from generation laser 801.

The transmitted component reaches detector 820, which is a silicon photodiode. The photodiode current is converted to a voltage using transimpedance amplifier 824, the output of which goes to lock-in amplifier 825. The output of lock-in 825 goes to a digital computer, which receives the signal and presents it to the user or other data collection systems. Lock-in 825 includes a frequency reference that is used to modulate laser driver 821, which provides a modulated drive output for generation laser 801.

The above discussion illustrates certain embodiments of the invention. Additional embodiments and variations of the described embodiments are possible, as would be apparent to the skilled artisan.

For example, one of the embodiments described above refers to the use of photoresist as an implant masking layer 11. However, other materials may be used, and may even be preferred for purposes of integrating the test structure formation into the process flow normally used for wafer fabrication. For example, the masking material may be deposited materials such as silicon dioxide, polysilicon and/or silicon nitride.

Certain embodiments are related to process control. However, other embodiments may be used for process development. For example, if a development engineer wants to compare the abruptness possible with different laser anneal treatments (e.g. wherein a laser beam is used to heat the silicon locally to activate dopant atoms this measurement can provide information. For this case, the possibilities for test structures are expanded, because it is no longer necessary to fit within a standard flow. For example, it is possible to use a mask of narrow poly lines, then put on spacers (silicon nitride layers on the side of the poly lines, as are commonly applied to polysilicon gates in transistors), then anneal before removing the mask to capture stress effects that the spacers may introduce. Other custom adaptations of structures for process development are limitless in possibility, but would employ one or more principles discussed above.

Figure 9:
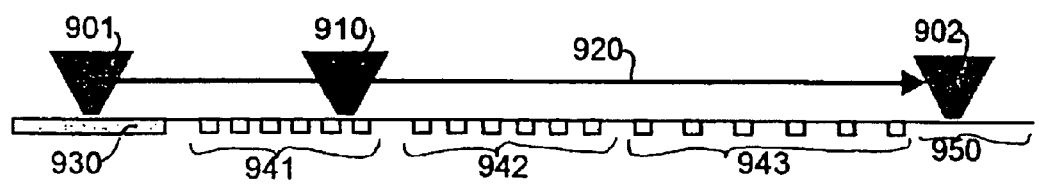
FIG. 9 illustrates, in a cross-sectional diagram, scanning across a structure with fully doped and undoped regions included.

In another embodiment, fully doped and undoped regions are included in the test pattern. As illustrated in FIG. 9, five test patterns, 930, 941, 942, 943 and 950 may be included in a test structure, whereas pattern 930 is a fully doped region (no stripe pattern, 100% doping). Pattern 950 is a fully undoped region (no ion implant, 0% doping). Patterns 941, 942 and 943 have constant width doped bars (also called "implanted regions") in each pattern, and increasing width undoped regions across the three patterns. Other embodiments can use other patterns or a different number of patterns. In this example, the dimensions before annealing (called the printed dimensions) are 0.1 μm bars and 0.1 μm spaces for pattern 941 (50% doped), 0.1 μm bars and 0.15 μm spaces for pattern 942 (40% doped), and 0.1 μm bars and 0.2 μm spaces for pattern 943 (33% doped).

Measurements of the type described above are made in positions over patterns 930, 941–943, and 950. For example, a first measurement is made over pattern 930. A laser beam at position 901 is then scanned along a horizontal line 920 to final measurement position 902 over pattern 950, with measurements taken at each of a number of positions along line 920. For example, five measurements may be made in the five regions containing patterns 930, 941, 942, 943 and 950. In another embodiment, a line scan consisting of a larger number of measurements is made, for instance 101 measurements in 100 fixed increment steps between position 901 and 902 along line 920. In one example, each pattern is 10 μm wide and the step size is 0.5 μm, to cover a 50 μm long pattern in 101 steps.

When a region of a wafer is illuminated by a beam and the reflected beam is measured, the measured signal is a superposition of the signals from the doped and undoped regions within the measurement region, given by the relation $$S = S_D \times F_D + S_U \times F_U \quad (7)$$

where S is the signal, $S_D$ and $S_U$ are signals from fully doped and undoped regions respectively, and $F_D$ and $F_U$ are the fraction of the measurement area that is doped and undoped respectively. Noting that the fraction of the measurement area that is doped and undoped is given by $$F_D = \frac{W_{PD} + 2\delta}{P} \quad (8)$$

$$F_U = \frac{W_{PU} - 2\delta}{P} \quad (9)$$

where δ is the lateral diffusion distance, P is the pitch (center-to-center spacing between bars), and $W_{PD}$ and $W_{PU}$ is the printed width of the doped and undoped regions respectively ($P = W_{PD} + W_{PU}$), the signal is written as $$S = S_D F_{PD} + S_U F_{PU} - \frac{2\delta}{P}(S_D - S_U) \quad (10)$$

where $F_{PD}$ and $F_{PU}$ are the printed fractions of the measurement area that are doped and undoped. By rewriting the above expression, the lateral diffusion is given by $$\delta = \frac{P}{2} \times \frac{S_D F_{PD} + S_U F_{PU} - S}{(S_D - S_U)} \quad (11)$$

The benefit of using a test structure such as that shown in FIG. 9 is that all the quantities in the above expression are known, so the lateral diffusion may be directly computed. Specifically, the pitch P is set by the lithographic mask and is known in advance. The printed doped and undoped fractions $F_{PD}$ and $F_{PU}$ are known either from the mask or from SEM measurements of the photoresist mask. The signal from the doped region, $S_D$, is found with the measurement made at position 930. The signal from the undoped region, $S_U$, is found with the measurement at position 950. Each region 941, 942 and 942 has different printed fractions $F_{PD}$ and $F_{PU}$ set by the pitch and doped bar width.

FIG. 10 illustrates a measured signal of one example varying as a function of the fraction of measurement area that is doped as printed. If there is no lateral diffusion, the signal follows line 1010. Point 1030 corresponds to the signal in the fully doped region 950 (which may, for example, be 2000 μV with a junction depth of 350 Å. Point 1050 corresponds to the signal in the fully undoped region 950, which may be 20,000 μV. The signals are indicated in the following table, for the cases of both zero lateral diffusion and 30 nanometers lateral diffusion.

| Region | Doped bar (nm) | Undoped (nm) | $F_D$ (%) | $F_U$ (%) | Signal (δ = 0) (uV) | Signal (δ = 30 nm) (uV) |
|---|---|---|---|---|---|---|
| 930 | N/A | 0 | 0 | 100 | 2,000 | 2,000 |
| 941 | 100 | 100 | 50 | 50 | 11,000 | 5,600 |
| 942 | 100 | 150 | 40 | 60 | 12,800 | 8,480 |
| 943 | 100 | 200 | 33 | 67 | 14,000 | 10,400 |
| 950 | 0 | N/A | 100 | 0 | 20,000 | 20,000 |

If there is no lateral diffusion, the points 1041*u*, 1042*u* and 1043*u* are measured at regions 941, 942 and 943. These points fall on a straight line connecting point 1050 (from a measurement over fully undoped region 950) to point 1030 (from a measurement over fully doped region 930). However, if there is lateral-diffusion, the corresponding points fall on a line with lesser slope, such as line 1020. This line 1020 connects points 1030, 1041*d*, 1042*d*, and 1043*d*, and intersects the vertical axis at point 1051, which is below point 1050. Lateral diffusion δ is found by substituting the signal from two of the three regions 941, 942 or 943 (signals 1041*d*, 1042*d*, or 1043*d*) into equation 11 above, The results may be found from one region, or averaged from several regions to improve accuracy.

Numerous such modifications, adaptations and variations of the embodiments described herein are encompassed by the attached claims.

What is claimed is:

1. A method for evaluating a semiconductor wafer, the method comprising:

forming a test structure of a predetermined geometry in the semiconductor material, said test structure comprising a plurality of areas separated from one another, at least one area in the plurality of areas having different properties as compared to another area in the plurality of areas;

measuring light reflected from said test structure, said reflected light having a component comprising a superposition of reflections of different amplitudes or phases from said areas with differing electronic properties;

analyzing a signal obtained from measuring to determine the extent of lateral diffusion in said region; and using the extent of lateral diffusion to accept or reject the semiconductor wafer for further processing.

2. The method of claim 1 further comprising:

illuminating at least a portion of the test structure with a first beam to generate a plurality of charge carriers;

illuminating with a second beam to perform said measuring in at least a region of the semiconductor wafer having at least some of the charge carriers in the plurality generated by the first beam.

3. The method of claim 2 wherein:

each of the first beam and the second beam are coincident.

4. The method of claim 2 wherein:

at least one of the first beam and the second beam is polarized.

5. The method of claim 4 wherein:

the test structure includes a plurality of doped regions, each doped region being separated from an adjacent doped region; and polarization is parallel to each of said doped regions.

6. The method of claim 4 wherein:

each of the first beam and the second beam is polarized.

7. The method of claim 2 further comprising:

modulating intensity of the first beam at a predetermined frequency; and using the predetermined frequency during said measuring.

8. The method of claim 1 wherein:

the test structure includes a plurality of doped regions.

9. The method of claim 8 wherein:

each doped region is separated from an adjacent doped region by a fixed distance.

10. The method of claim 8 wherein:

each doped region is separated from an adjacent doped region by a different distance.

11. The method of claim 1 wherein:

the test structure is a first test structure comprising a plurality of first doped regions separated each from another by a first distance;

the method further comprises forming in the semiconductor wafer a second test structure comprising a plurality of second doped regions separated each from another by a second distance different from the first distance; and the method further comprises repeating the acts of illuminating and measuring with the second test structure.

12. A method for evaluating a semiconductor wafer, the method comprising:

forming a test structure of a predetermined geometry in the semiconductor wafers;

measuring a signal indicative of a dimension of the test structure; and changing a process parameter used in fabrication of the wafer, depending on said signal obtained from said measuring.

13. The method of claim 12 further comprising:

illuminating the test structure with at least one beam of electromagnetic radiation.

14. The method of claim 13 wherein:

said beam is polarized.

15. The method of claim 12 further comprising:

illuminating the test structure with a first beam to generate a plurality of charge carriers; and illuminating the test structure with a second beam to sense a concentration of the charge carriers generated by the first beam.

16. The method of claim 15 wherein;

the first beam is modulated at a predetermined frequency; and said predetermined frequency is used during said act of measuring.

17. An apparatus for evaluating a semiconductor wafer, the apparatus comprising:

means for forming a test structure of a predetermined geometry in the semiconductor wafer; and means for measuring a signal indicative of dimension of the test structure.

18. The apparatus of claim 17 further comprising:

means for illuminating the test structure with a beam of electromagnetic radiation.

19. The apparatus of claim 18 further comprising:

means for modulating coupled to said means for illuminating; and a lock-in amplifier coupled to said means for measuring.

* * * * *